US00PP22246P3

(12) United States Plant Patent
Hamilton et al.

(10) Patent No.: US PP22,246 P3
(45) Date of Patent: Nov. 15, 2011

(54) RASPBERRY PLANT NAMED 'DRISRASPTWO'

(50) Latin Name: ***Rubus idaeus* L.**
Varietal Denomination: DrisRaspTwo

(75) Inventors: Brian K. Hamilton, San Jose, CA (US); José Jesús Renteria, Watsonville, CA (US); Richard E. Harrison, Aptos, CA (US); Lluvia V. Gutierrez, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/592,358

(22) Filed: Nov. 24, 2009

(65) Prior Publication Data

US 2011/0126332 P1 May 26, 2011

(51) Int. Cl.
*A01H 5/00* (2006.01)

(52) U.S. Cl. ..... Plt./204

(58) Field of Classification Search ..... Plt./204
See application file for complete search history.

*Primary Examiner* — June Hwu
(74) *Attorney, Agent, or Firm* — Jondle & Associates, P.C.

(57) ABSTRACT

This invention relates to a new and distinct variety of raspberry plant named 'DrisRaspTwo' which is primarily characterized by medium-sized, medium-red fruit that mature to a dark red color and having an early bud burst, is disclosed.

2 Drawing Sheets

Genus and species: *Rubus idaeus* L.
Variety denomination: 'DrisRaspTwo'.

BACKGROUND OF THE NEW PLANT

The present invention relates to a new and distinct raspberry cultivar designated 'DrisRaspTwo' and botanically known as *Rubus ideaus* L. This new raspberry variety was discovered in Santa Cruz, Calif. in May 2004 and originated from a cross between the female parent raspberry plant 'Driscoll Cardinal' (U.S. Plant Pat. No. 14,903) and the proprietary male parent raspberry plant 'W776.1' (unpatented). The original seedling of the new cultivar was asexually propagated by stolons or tissue culture, at a nursery in Santa Cruz, Calif. 'DrisRaspTwo' was subsequently asexually propagated and underwent further testing at a nursery in Santa Cruz, Calif. for five years. The present invention has been found to be stable and reproduce true to type through successive asexual propagations.

SUMMARY OF THE INVENTION

The following are the most outstanding and distinguishing characteristics of this new cultivar when grown under normal horticultural practices in Santa Cruz, Calif.

1. Medium-sized, medium-red fruit that mature to a dark red color; and
2. Having an early bud burst.

DESCRIPTION OF THE PHOTOGRAPHS

This new raspberry plant is illustrated by the accompanying photographs which show the fruit of the plant as well as the primocanes; the colors shown are as true as can be reasonably obtained by conventional photographic procedures. The photographs are of plants that are 2 years old.

DESCRIPTION OF THE NEW VARIETY

Figure 1:
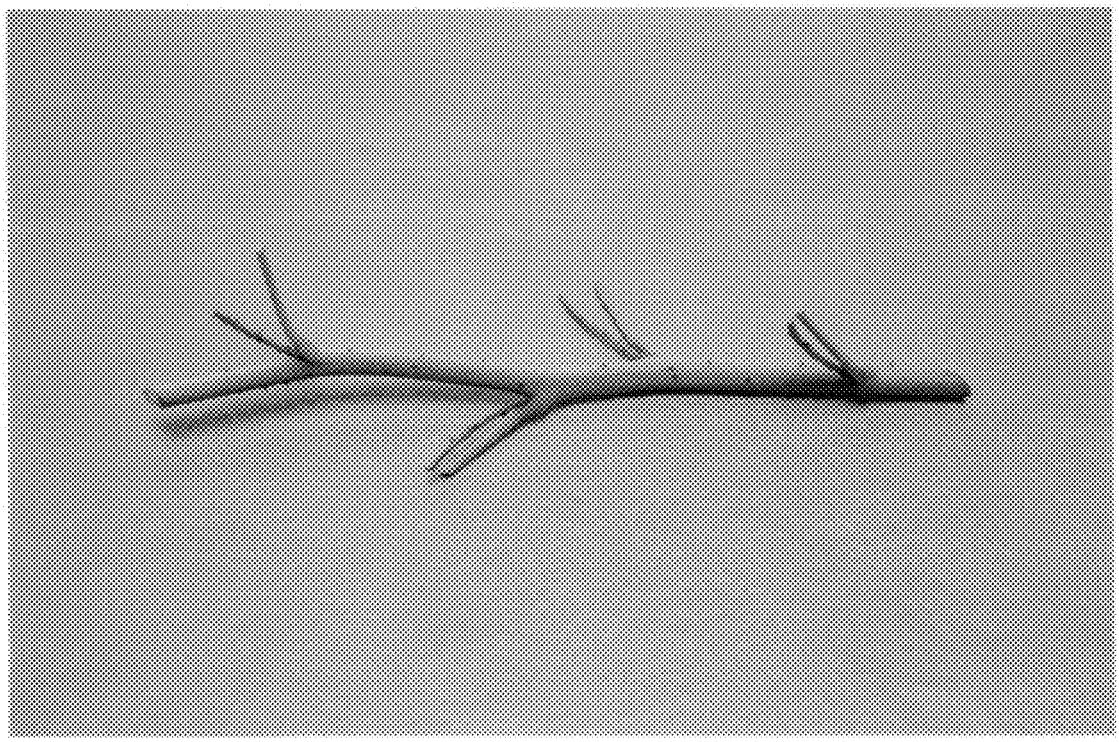
FIG. 1 shows a section of a young cane with prickles.
Figure 2:
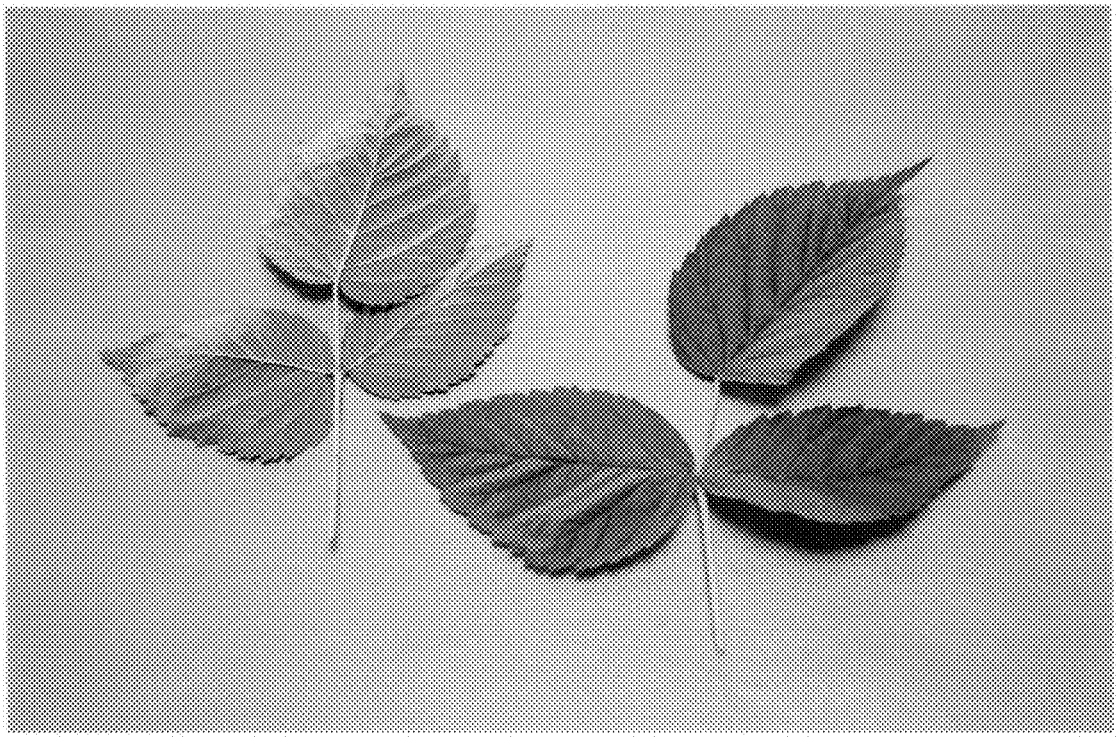
FIG. 2 shows both the upper surface and the lower surface of the plant leaves.
Figure 3:
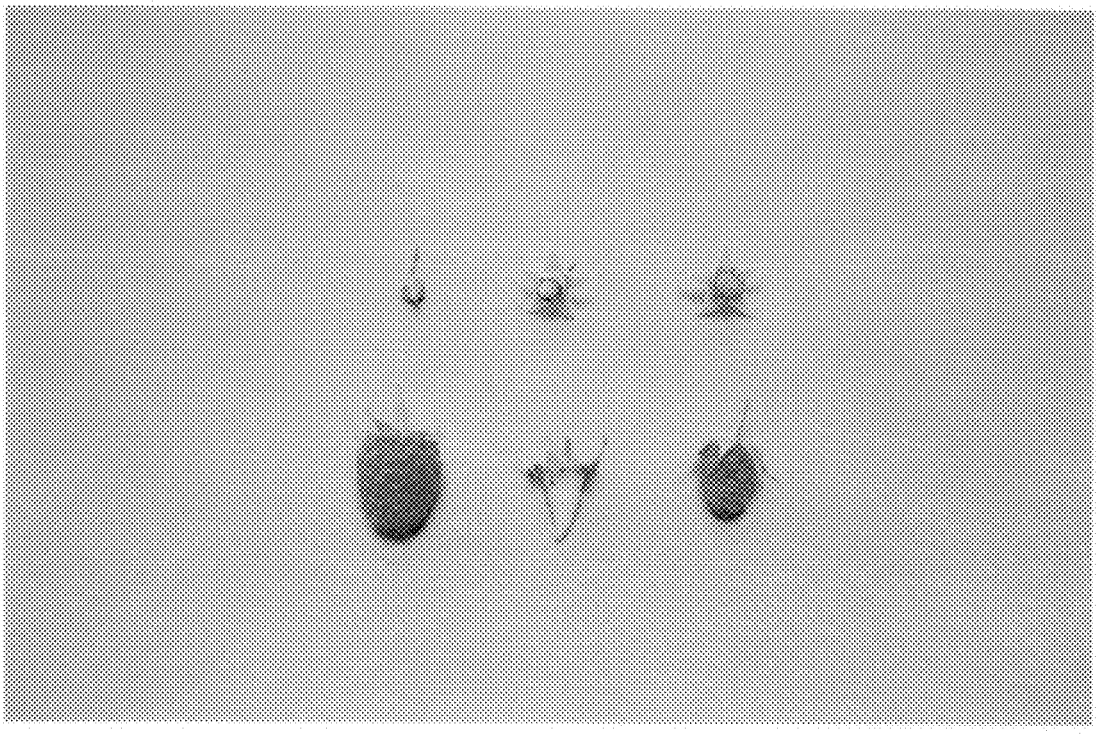
FIG. 3 shows (from left to right, from top to bottom) a flower bud, an immature fruit, an immature fruit, a mature fruit, the fruit plug, and immature fruit.

The following description of 'DrisRaspTwo' is based on observations taken from the 2005 to 2009 growing seasons in Santa Cruz, Calif. This description is in accordance with UPOV terminology. Color designations, color descriptions, and other phenotypical descriptions may deviate from the stated values and descriptions depending upon variation in environmental, seasonal, climatic and cultural conditions. 'DrisRaspTwo' has not been observed under all possible environmental conditions. Color terminology follows The Royal Horticultural Society Colour Chart, London (R.H.S.) (2001 edition).

DETAILED BOTANICAL DESCRIPTION

Classification:
- *Family.*—Rosaceae.
- *Botanical.*—*Rubus idaeus* L.
- *Common name.*—Raspberry.
- *Variety name.*—'DrisRaspTwo'.

Parentage:
- *Female parent.*—The raspberry Plant 'Driscoll Cardinal' (U.S. Plant Pat. No. 14,903).
- *Male parent.*—The proprietary raspberry plant 'W776.1' (unpatented).

Plant:
- *Propagation.*—Tissue culture and root cuttings Self-fruitful.
- *Time of bud burst.*—Early.
- *Height.*—198.4 cm.
- *Width.*—219.2 cm.

*Length/width ratio.*—0.9.
*Hardiness zone.*—Tested in zones 9b-10a.

Primocane fruiting:
*Length* (4$^{th}$ *lateral from tip*).—85.7 cm.
*Number of fruit per lateral.*—30.
*Harvest season.*—Early September to mid-October.

Primocanes:
*Number of young shoots.*—Medium.
*Time of young shoot emergence from the soil.*—Early.
*Glaucosity* (*waxy bloom*).—Weak.
*Shape of cane cross section.*—Rounded to angular.
*Prickles* (*spines*).—Length: Short. Color: RHS 182A (Medium greyed-red). Density of spines on central third: Medium. Attitude of tip: Downward. Texture: Soft. Presence and distribution on petioles: Present and regularly distributed. Pubescence on canes: Present. Internodal distance at central third of cane: 5.3 cm.

Floricane fruiting:
*Harvest season.*—Mid-May to late June.

Leaves:
*Type.*—Compound; 3 leaflets.
*Arrangement.*—Free.
*Leaf color.*—Upper surface: RHS 137A (Medium green). Lower surface: RHS 148B (Medium yellow-green).
*Relief between the veins.*—Medium.
*Glossiness.*—Medium.
*Petiolule length.*—4.0 mm.
*Lateral leaflet adjacent to terminal leaflet.*—Length: 3.9 cm. Width: 1.19 cm
*Petiole color.*—Both surfaces: RHS 144C (Medium yellow-green).
*Number of leaflets.*—Usually three.
*Overlapping of leaflets.*—Touching.
*Lateral leaflet* (*length to stalklet, lower pair*).—Short.
*Terminal leaflet.*—Length: 15.5 cm. Width: 10.7 cm. Lateral leaflets (basal pair): Length: 10.2 cm. Width: 7.5 cm. Rachis length between the terminal leaflet and adjacent lateral leaflet: 4.4 cm. Relief between the veins: Medium.

Stipules:
*Orientation.*—Erect.

Flowers:
*Diameter.*—3.99 cm.
*Size.*—Medium.
*Color.*—RHS 155B (White).
*Length/width ratio.*—1.9.
*Petal.*—Length: 0.95 cm. Width: 0.49 cm.
*Pedicel.*—Length: 2.73 mm. Width: 0.78 mm.
*Peduncle.*—Presence of anthocyanin coloration: Absent. Intensity of anthocyanin coloration: Absent.

Fruit:
*Immature fruit color.*—RHS 43B (Medium red).
*Maturing fruit color.*—RHS 45B (Medium red).
*Mature fruit color.*—RHS 46A (Dark red).
*Shape.*—Circular.
*Drupelet.*—Size: Medium. Average number per fruit: 77.
*Glossiness.*—Medium.
*Size.*—General: Medium. Length: 3.14 cm. Width: 2.97 cm. Ratio of length to width: As long as broad.
*Soluble solids* (% *in Brix*).—10.4.
*Titratable acidity* (% *as citric acid*).—11.1.
*Firmness.*—Medium.
*Adherence to plug.*—Medium.
*Main bearing type.*—3 (both on previous year's cane in summer and on current year's cane in autumn.

Disease and insect resistance: Good tolerance has been observed to typical raspberry pests and diseases.

COMPARISON WITH PARENTAL AND COMMERCIAL VARIETIES

'DrisRaspTwo' differs from the female parent 'Driscoll Cardinal' (U.S. Plant Pat. No. 14,903) in that the time of bud burst for 'DrisRaspTwo' is early, while the time of bud burst for 'Driscoll Cardinal' is late. The number of fruit per lateral (primocane) for 'DrisRaspTwo' is 30, while the number of fruit per lateral for 'Driscoll Cardinal' is 19. Additionally, 'DrisRaspTwo' has pubescence on the primocane prickles, while 'Driscoll Cardinal' does not.

'DrisRaspTwo' differs from the proprietary male parent 'W776.1' (unpatented) in that the fruit of 'DrisRaspTwo' is more tart than the fruit of 'W776.1'.

'DrisRaspTwo' differs from the commercial variety 'DrisRaspOne' (U.S. Plant Pat. No. 19,656) in that the time of bud burst for 'DrisRaspTwo' is early, while the time of bud burst for 'DrisRaspOne' is late. 'DrisRaspTwo' has larger fruit (length is 3.14 cm and width is 2.97 cm) than 'DrisRaspOne' (length is 2.94 cm and width is 2.70 cm). Additionally, the titratable acidity (expressed as a percentage of citric acid) for 'DrisRaspTwo' is 11.1, while the titratable acidity for 'DrisRaspOne' is 15.3.

I claim:

1. A new and distinct cultivar of raspberry plant as described and shown herein.

* * * * *